United States Patent
Kanipayor et al.

(10) Patent No.: US 6,465,242 B1
(45) Date of Patent: Oct. 15, 2002

(54) PORTABLE INCUBATOR

(75) Inventors: Ravi Kanipayor, London; Ron Emburgh, Mississauga, both of (CA)

(73) Assignee: Aquasure Technologies Inc., London (CA)

( * ) Notice: Subject to any disclaimer, the term of this patent is extended or adjusted under 35 U.S.C. 154(b) by 37 days.

(21) Appl. No.: 09/599,581

(22) Filed: Jun. 22, 2000

(51) Int. Cl.⁷ ............................................. C12M 1/38
(52) U.S. Cl. ............................ 435/288.1; 435/286.1; 435/303.1; 435/809; 422/99; 422/102; 219/386; 219/407; 219/432
(58) Field of Search ...................... 435/286.1, 288.1, 435/288.2, 288.3, 303.1, 304.1, 304.2, 304.3, 809, 307.1; 422/99, 102, 104; 219/386, 407, 438, 432, 437; 215/10; 206/509

(56) References Cited

U.S. PATENT DOCUMENTS

| | | | |
|---|---|---|---|
| 2,187,888 A | * | 1/1940 | Nachumsohn |
| 2,686,250 A | * | 8/1954 | Schroeder |
| 2,784,146 A | | 3/1957 | Goldman ...................... 195/100 |
| 3,039,938 A | | 6/1962 | Charm ......................... 195/139 |
| 3,103,162 A | * | 9/1963 | Scofield |
| 3,374,917 A | * | 3/1968 | Troy ............................ 206/504 |
| 3,391,824 A | * | 7/1968 | Wiseman ..................... 206/504 |
| 3,562,114 A | | 2/1971 | Steidl et al. ................. 195/139 |
| 3,607,134 A | | 9/1971 | McIntyre ....................... 23/292 |
| 3,660,242 A | * | 5/1972 | Gordon et al. |
| 3,808,825 A | * | 5/1974 | Ciurea |
| 3,931,494 A | * | 1/1976 | Fisher et al. |
| 4,256,697 A | | 3/1981 | Baldwin ...................... 422/104 |
| 4,691,828 A | * | 9/1987 | Slusarczyk et al. ......... 206/509 |
| 4,700,050 A | * | 10/1987 | Hennuy et al. |
| 4,840,771 A | | 6/1989 | Williamson et al. ......... 422/104 |
| 4,906,566 A | | 3/1990 | Cullimore et al. ............ 435/34 |
| 5,252,484 A | | 10/1993 | Matner et al. ............... 435/288 |
| 5,650,290 A | | 7/1997 | Grant .......................... 435/34 |
| 5,896,811 A | * | 4/1999 | Yaow et al. |
| 5,903,710 A | | 5/1999 | Wefler et al. ................ 392/392 |

* cited by examiner

*Primary Examiner*—William H. Beisner
(74) *Attorney, Agent, or Firm*—Bereskin & Parr

(57) ABSTRACT

A portable incubator for testing water comprising a housing, a heating element, a temperature sensor, a heating controller and a specimen bottle having recesses for receiving the heating element and the temperature sensor. The specimen bottle is filled with water to be tested which is mixed with a reagent and placed inside the incubator. The heating controller serves to keep the temperature of the water within a preset range.

10 Claims, 4 Drawing Sheets

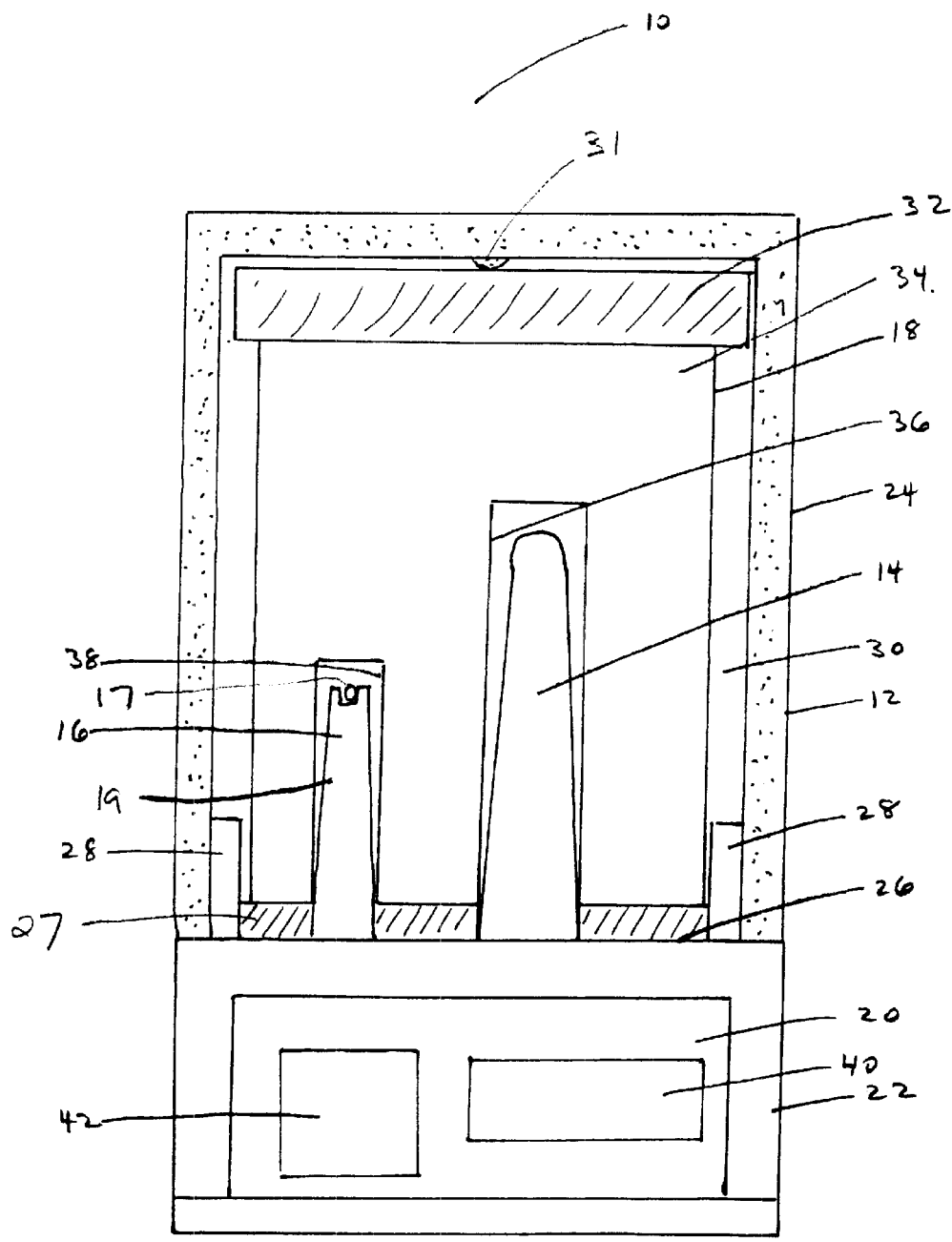

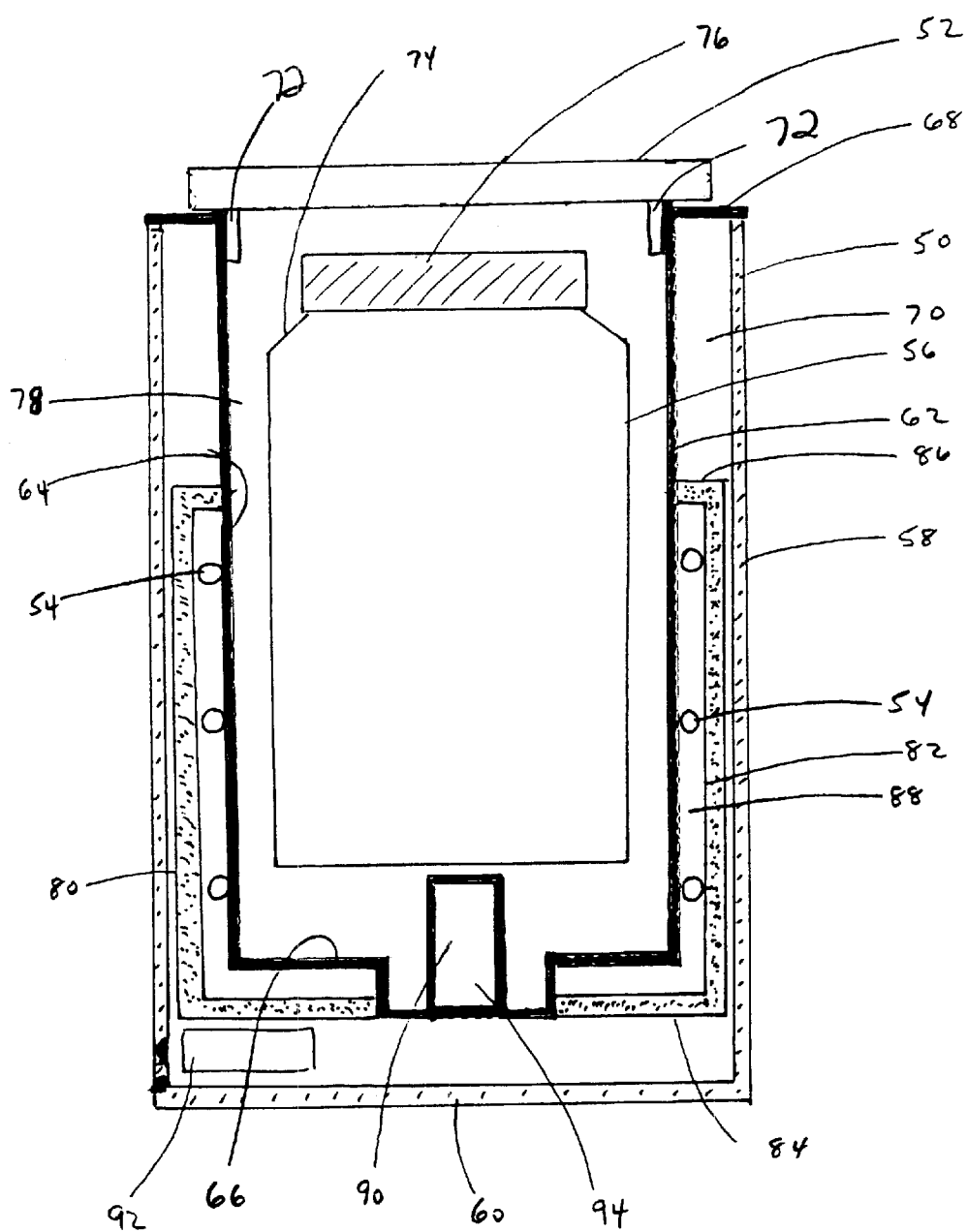

PORTABLE INCUBATOR

FIELD OF THE INVENTION

This invention relates to an apparatus for testing water samples, and more particularly to portable incubators for testing water samples outside the laboratory setting.

BACKGROUND OF THE INVENTION

Water quality is an issue that has become of increasing concern to people in North America and around the world. Bottled water sales and water purification system sales have increased greatly in the past twenty years as consumers place less trust in the water obtained from their taps and wells. Generally, people are concerned about pollutants and harmful microbes in their tap water. Many homes in rural areas around the world obtain their water from wells located on the homeowner's property. The quality of water from these wells can be compromised due to runoff from farm properties and natural disasters such as earthquakes, floods etc.

Some jurisdictions require that the water be tested on construction of a well. Other jurisdictions provide water testing for private well water on a regular basis either free of charge or for a fee to homeowners.

At present the microbial testing of water samples from wells is done in a large incubator in a laboratory. Homeowners obtain a small sterile bottle from a laboratory and fill it with water obtained from their well or tap and take the water sample in to a centralized testing laboratory. The laboratory prepares the sample with a reagent and places it with other water samples in a large sealed incubator. A heating element is activated to a desired temperature and the air within the incubator is heated over a period of many hours to encourage the growth of any microbes in the water. If there are microbes in a given water sample, the reagent will change the color of the water sample to indicate their presence. The laboratory will then inform the homeowner of the results of the test generally within a week to ten days.

There are a number of disadvantages to this method of water testing. The process is very time-consuming and it can take many days to detect a water quality problem. In that time, the homeowner may be consuming microbes threatening their health.

The process is also inconvenient and lends itself to infrequent testing. The homeowner must first obtain a sterile bottle from a laboratory and transport the collected water sample in the sterile bottle from their home to the laboratory which may be far away. As well, the sample must be delivered to the laboratory in a cool condition (around 4° C.) in a timely manner to keep the microbes in a viable state for the test to be meaningful and provide a valid test result. As a result of the time, effort and cost involved, homeowners are not testing their water as frequently as they should. It is also costly for the government to purchase and maintain the incubator and to provide testing services to the general public.

In addition, there are problems with the lab environment. Multiple handling of the sample can increase potential errors. Further delays occur when laboratories perform batch testing rather than running individual samples immediately when they are received. Clerical errors and time delay can jeopardize the health of those people whose wells are being tested.

Accordingly, there is a need for a portable water sample testing apparatus that is inexpensive, convenient and accurate. Such an apparatus should be designed to be small and easy to operate by non-technical personnel.

SUMMARY OF THE INVENTION

In one aspect, the invention provides a portable incubator for heating fluids comprising:
a) a housing;
b) at least one heating element positioned within the housing;
c) a specimen container positioned within the housing having at least one recess for receiving the at least one heating element.

In another aspect the invention provides a portable incubator comprising:
a) a housing;
b) a specimen container placed within said housing;
c) a heating element located proximal to said specimen container;
d) a heating controller for controlling the heating element, the heating controller maintaining the temperature of the air within the incubator within a preset range.

In another aspect the invention provides a specimen bottle for water testing comprising:
(a) a bottle section, the bottle section having at least one recess for receiving a heating element and at least one recess for receiving a temperature sensor;
(b) a removable cap for sealing the specimen bottle; and
(c) a reagent for microbial testing.

BRIEF DESCRIPTION OF THE DRAWINGS

The invention will now be described, by way of example only, with reference to the following drawings, in which:

FIG. 2 is a sectional front-view of the incubator taken along line 2—2 of FIG. 1;

FIG. 3 is a sectional front-view of an alternative embodiment of portable incubator in accordance with the present invention.

DETAILED DESCRIPTION

Figure 1:
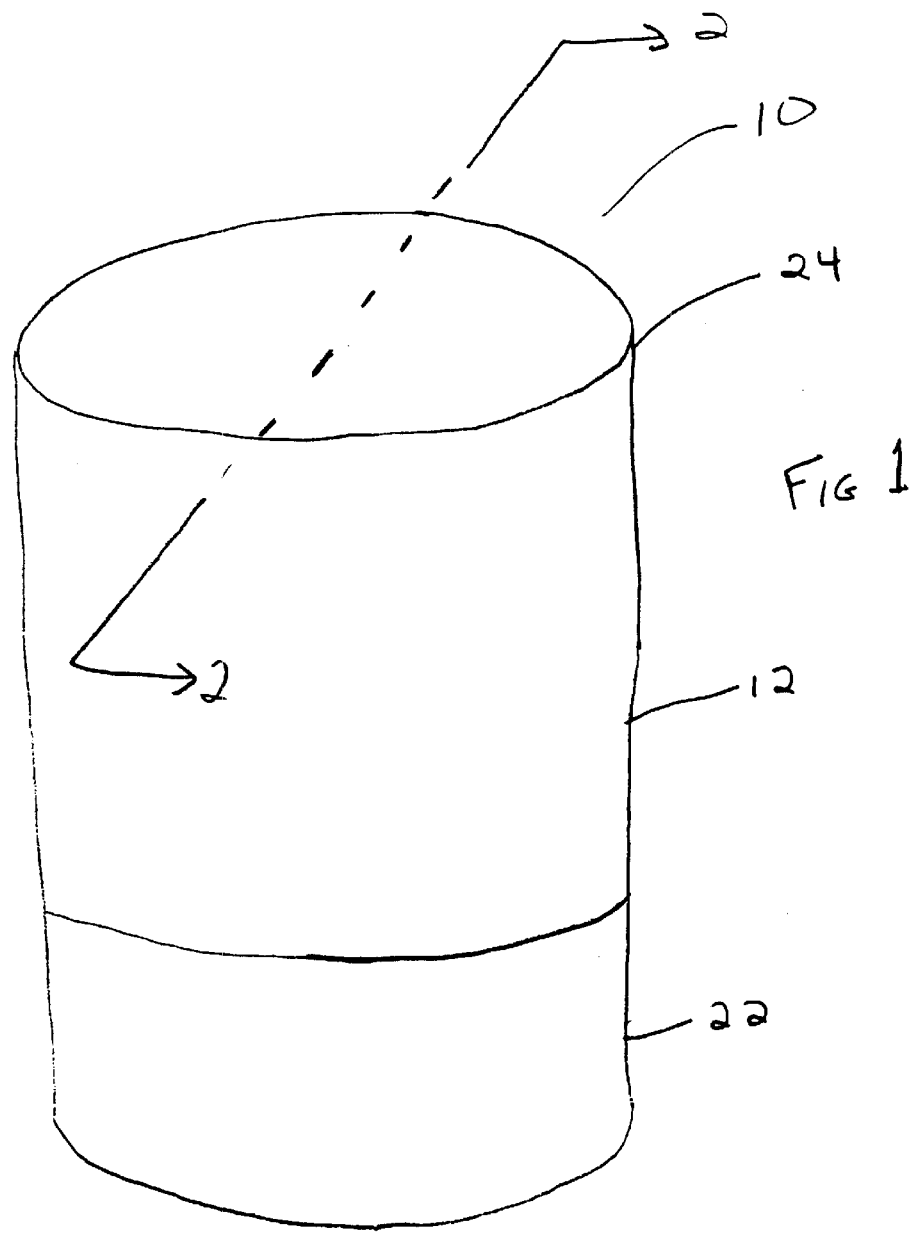
FIG. 1 is a perspective view of a portable incubator in accordance with the present invention.

Referring generally to FIGS. 1 and 2, illustrated therein is a portable incubator 10 made in accordance with a preferred embodiment of the present invention. Portable incubator 10 comprises a housing 12, a heating element 14, a temperature sensor 16, a specimen container 18 and a control chamber 20.

Housing 12 is a generally cylindrical enclosure comprising a base enclosure 22 and a removable cap 24. Optionally, housing 12 is insulated. Base enclosure 22 defines a cylindrical control chamber 20 and one end of base enclosure 22 comprises an incubation wall 26. Incubation wall 26 is provided with an open-ended cylindrical lip 28 extending outwardly from control chamber 20. Cylindrical lip 28 has an outer diameter that is preferably less than the outer diameter of base enclosure 22. Removable cap 24 is generally cylindrical having a closed top. Removable cap 24 is placed such that the open end of the cap fits snugly around cylindrical lip 28. When so placed, removable cap 24 and incubation wall 26 define an incubation chamber 30. Removable cap 24 is optionally provided with a pressure ball 31 mounted on the inside of the uppermost surface of removable cap 24. Incubation wall 27 is provided with a foam base 27 with suitable apertures for temperature sensor 16 and heating element 14. As well, removable cap 24 may be a thermally efficient cap such as a double walled cap with a vacuum or inert gas between the double walls. Such a cap would slow the rate of heat transfer to the environment. As well, A heating element 14 is mounted on incubation wall 26. Heating element 14 as shown in FIG. 2 is a tapered and elongated member although any shape may be used. Heating element 14 extends upward through a substantial portion of incubation chamber 30.

A temperature sensor 16 also extends upwardly from incubation wall 26. Temperature sensor 16 as shown in FIG. 2 is generally elongated and tapered. Preferably, temperature sensor 16 is capable of reading temperatures to within 0.1° C. Temperature sensor 16 may comprise a thermistor 17 mounted on the top of a sleeve 19.

Specimen container 18 comprises a specimen cap 32 and a specimen bottle 34. Specimen bottle 34 is generally cylindrical with heating cavity 36 and sensor cavity 38 to allow for the placement of heating element 14 and temperature sensor 16 respectively proximal to any liquid within specimen container 18. Heating cavity 36 is designed to allow for a very small air gap between heating element 14 and the outer wall of heating cavity 36 for efficient transfer of heat to the sample. Similarly, sensor cavity 38 is designed to allow for a very small air gap between temperature sensor 16 and the outer wall of sensor cavity 38 so as to obtain an accurate sample temperature.

Control chamber 20 further comprises a power source 40 and a heating element controller 42. Power source 40 may be a battery or may comprise an electrical input from a power cord or may be any other suitable power source known in the art.

Heating element controller 42 serves to control the operation of heating element 14 and obtain temperature readings from temperature sensor 16. Optionally, heating element controller also further comprises a timer (not shown) for measuring the time since the start of a test and for shutting off power to heating element 14 at the end of a preset time. Heating element controller 42 is designed to keep the temperature of the water in specimen container 18 within a preset range. For coliform testing in water, a pre-set temperature of 35° C. with a range of +/−0.5° C. is preferable.

In use, specimen cap 32 is detached from specimen bottle 34 and water, or any other liquid to be tested, is placed within specimen bottle 34. An appropriate reagent is dissolved in the water. The reagent is preferably a chemical designed to change the color of the water in the water sample to indicate the presence or absence of microbes. Examples of such reagents are 1) IDEXX—Colilert®
2) HACH—MEL P/A
3) EBPI—ColiBag™
4) VLPI—PurTest™ Bacteria Specimen cap 32 is then fastened to specimen bottle 34.

Removable cap 24 is removed from incubator 10 by twisting removable cap 24 off cylindrical lip 28. Specimen container 18 is then placed within incubation chamber 30 with heating element 14 and temperature sensor 16 fitting within heating cavity 36 and sensor cavity 38 respectively. Removable cap 24 is put back on incubator 10 and pressure ball 31 serves to press specimen container 18 into foam base 27. The base of heating cavity 36 fits snugly around the base of heating element 14, while the base of sensor cavity 38 fits snugly around the base of temperature sensor 16.

Heating element controller 42 is then activated, causing heating element 14 to be heated to a temperature above that of the desired temperature of the water to be tested. Heating element 14 heats the air in the gap between heating element 14 and specimen bottle 34 and which in turn heats the liquid within specimen container 18. Because the air gap between heating element 14 and heating cavity 34 is so small, and because of the snug fit of heating element 14 in the base of heating cavity 36, almost all of the heat energy produced by heating element 14 is transferred to the water in specimen bottle 32. Since heating element 14 protrudes deep into specimen container 18, the sample is heated efficiently from the inside.

Temperature sensor 16 serves to read the temperature of the air between sensor cavity 38 and temperature sensor 16 which is heated by the water within specimen container 18. Because the air gap between temperature sensor 16 and sensor cavity 36 is so small, the fact that air changes temperature much faster than water and the fact that temperature sensor 16 reads the temperature near the centre of specimen bottle 34, the temperature of the water is quickly reflected in the air gap and the temperature read by temperature sensor 16 will closely approximate the temperature of the water in specimen bottle 32.

Heating element controller 42 obtains the temperature reading from temperature sensor 16. When the temperature of the water within specimen bottle 34 reaches a preset level, heating element controller 42 deactivates heating element 14. Temperature sensor 16 continues to read the temperature of the water within specimen container 18. When the temperature of the water within specimen container 18 falls to a second preset level, heating element controller 42 activates heating element 14 to heat the water within specimen container 18. Thus, the water within specimen container 18 is heated to within a preset temperature range. If temperature sensor 16 is a thermistor capable of reading temperature to +/−0.1° C., then the temperature range of the water in specimen bottle 34 may be kept to within +/−0.1° C. of a desired temperature. This degree of precision will improve the accuracy of the water test.

The water sample is heated in this fashion for a number of hours in order to encourage the growth of any microbes in the water sample. After a preset time, specimen container 18 is removed from incubator 10 and the color of the water is observed. After the water has been heated for a preset time, the power can be manually shut off or, optionally, a timer will shut off power source 40. Any microbes in the water will react with the reagent and cause a color change in the water by this preset time. Optionally, a visible or audible signal is activated by the timer indicating that the preset time has passed.

It will be appreciated that incubator 10 may be provided with multiple heating elements and that specimen container 18 may be provided with multiple cavities to receive those heating elements. As well, the spatial configuration of the various elements of the incubator may be altered significantly without departing from the present invention. For example, the incubator may be configured for side loading of the specimen bottle with heating elements extending sideways into cavities in the specimen bottle. As well, control chamber 20 and the elements therein may be separated from the main incubator or reoriented within incubator 10.

As well, it will also be appreciated that this design may be adapted to test multiple samples within multiple specimen containers using the same temperature controller and/or power source.

In an alternative embodiment to the present invention shown in FIG. 3, portable incubator 10 comprises a housing 50, a lid 52, a resistance heater 54 and a specimen container 56.

As shown in FIG. 3, housing 50 comprises cylindrical side wall 58 and base 60. Housing 50 is optionally insulated. Within housing 50 is an inner wall 62 comprising cylindrical incubation side wall 64, incubation base 66 and an annular flange 68. Annular flange 68 extends outwardly from the open top of incubation side wall 64. Inner wall 62 is placed such that the outer edge of annular flange 68 rests on the top of side wall 58. An air gap 70 separates side wall 58 from incubation side wall 64 and base 60 from incubation base 66.

Inner wall 62 is preferably a thin walled plastic for good heat transfer.

Lid 52 is a flat circular member having a cylindrical lip 72 extending downwardly therefrom. Cylindrical lip 72 is designed to fit snugly inside the top of incubation side wall 64. In a variant to the present invention, lid 52 may be a threaded cap designed to screw on to housing 50. As well, lid 52 is optionally insulated.

Specimen container 56 may be any standard specimen container known in the art having a specimen bottle 74 and a specimen cap 76. Specimen container 56 is designed to fit inside inner wall 62 leaving a minimal inner air gap 78.

A heater housing 80 is located within air gap 70 and is a generally cylindrical member having a heater housing side wall 82, a heater housing base 84 and an annular lip 86. Heater housing 80 is mounted on the outside of inner wall 62 such that a small resistor gap 88 is formed between the outer surface of inner wall 62 and the inner surface of heater housing 80. Resistance heater 54 is placed within heater housing 80 in the resistor gap 88. Resistance heater 54 may comprise a resistor, resistor wire, resistor coil, resistor foil, etc. In the case of resistor wire 54 shown in FIG. 3, the length of the resistor wire is dictated by the desired temperature and the ohms per foot rating of the resistor wire.

Within air gap 70 there is also provided a control chamber 90. Control chamber 90 houses a heating controller 94 and may optionally also have a timer (not shown). Resistance heater 54 is connected to a power source 92 and heating controller 94. Power source 92 may be an electrical input from a power cord or a battery. Heating controller 94 may be a bimetal switch placed between power source 92 and resistance heater 54. The bimetal switch is preferably chosen to open and cut off electrical contact between power source 92 and resistance heater 54 when the air within control chamber 90 reaches a preset temperature. If the temperature falls below a preset level, the bimetal switch will close and reconnect electrical contact with power source 92 allowing resistance heater 54 to be powered.

In use, specimen bottle 74 is filled with water to be tested and an appropriate reagent is dissolved in the water. Specimen bottle 74 is closed with specimen cap 76 and placed within inner wall 62 leaving a small inner air gap 78 between specimen bottle 74 and inner wall 62. Lid 52 is then placed on incubator 10 with cylindrical lip 72 fitting snugly inside the top of incubation side wall 64. Power source 92 is activated and power flows to resistance heater 54. Resistance heater 54 heats up as a result and the air within inner air gap 78 is heated as well. As a result of heat transfer from the air through specimen bottle 74 into the water, the temperature of the water rises. The efficiency of the heat transfer to the water sample inside specimen bottle 74 is dictated by the plastic material of wall 64 and its thickness, the heat loss at the junction of lip 72 and cap 52 and the insulation efficiency of the incubator chamber 58. When the temperature of the air within control chamber 90 reaches a preset level (which is reflected in the temperature of the air in air gap 78), heating controller 94 disconnects resistance heater 54 from power source 92. When the temperature falls below a second preset temperature, heating controller 94 reconnects power source 92 and resistance heater 54 and the air is heated. Thus, the water within specimen container 56 is maintained within a preset temperature range.

After the water has been heated for a preset time, the power can be manually shut off or, optionally, a timer will shut off power source 92. Any microbes in the water will react with the reagent and cause a color change in the water by this preset time. Optionally, a visible or audible signal is activated by the timer indicating that the preset time has passed.

It will be appreciated that in the embodiment shown in FIG. 3, specimen bottle 74 may be provided with a sensor cavity similar to that found in specimen bottle 34 of FIG. 2 for receiving control chamber 90 or heating controller 94 so as to obtain more precise temperature readings.

Figure 4:
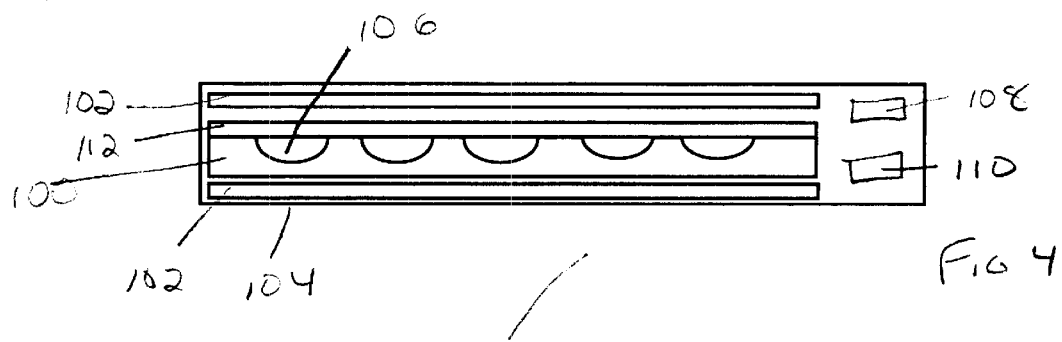
FIG. 4 is a sectional view of a third embodiment of portable incubator in accordance with the present invention.

FIG. 4 shows a third embodiment of the invention. Incubator 98 comprises a sample tray 100, resistance heater 102, a housing 104, power source 108 and temperature controller 110.

Figure 5:
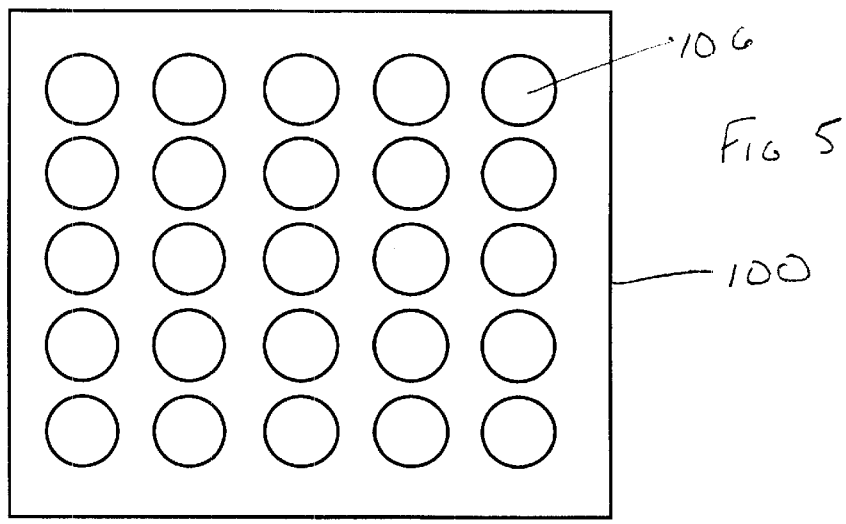
FIG. 5 is a top view of a sample tray for the incubator of FIG. 4.

Sample tray 100 is shown in greater detail in FIG. 5. It is a rectangular tray comprising rows of microcups 106 for receiving water to be tested. Sample tray 100 is placed within housing 104 between two flat layers of resistance heater 102. Resistance heater 102 may be a resistance foil, resistance wire etc. Resistance heater 102 is connected to temperature controller 108 which is in turn connected to power source 110. Temperature controller 108 may comprise a thermistor or a bimetal switch as described above. Power source 110 may comprise any power source described above.

In use, water to be tested is mixed with an appropriate reagent and poured into microcups 106. Sample tray 100 is placed within housing 104 between the layers (or coils as the case may be) of resistance heater 102. Sample tray 100 is optionally covered with a tray cover 112. Power source 110 is activated and power flows to resistance heater 102, heating the air within housing 104 and the water in microcups 106. Temperature controller 110 serves to maintain the temperature of the water within a preset range as described in the above embodiments. After a preset time has elapsed, sample tray 100 is removed from housing 104 and the water in the microcups is observed. By counting the number of microcups in which the water has changed color, a tester can determine not only that microbes are present in the sample, but the level of microbial contamination. This apparatus would be useful in situations where levels of contamination are important such as water testing at beaches.

It is to be understood that what has been described are preferred embodiments to the invention. The invention nonetheless is susceptible to certain changes and alternative embodiments fully comprehended by the spirit of the invention as described above, and the scope of the claims set out below.

We claim:

1. A portable incubator for heating fluids comprising:
   (a) a housing;
   (b) at least one heating element positioned within the housing;

(c) a specimen container positioned within the housing having at least one recess for receiving the at least one heating element; and (d) a temperature sensor mounted proximate to the specimen container;

(e) wherein the specimen container further comprises a recess for receiving the temperature sensor.

2. A portable incubator as claimed in claim 1 further comprising a control system for controlling the operation of the at least one heating element.

3. A portable incubator as claimed in claim 2 wherein the control system deactivates the at least one heating element when the fluid in the specimen container reaches a preset temperature.

4. A portable incubator as claimed in claim 3 wherein the control system activates the at least one heating element when the fluid in the specimen container falls below the preset temperature.

5. A portable container as claimed in claim 4 wherein the preset temperature is variable.

6. A portable incubator as claimed in claim 1 wherein the portable incubator is powered by a battery.

7. A portable incubator as claimed in claim 1 wherein the at least one heating element is substantially surrounded by the fluid.

8. A portable incubator as claimed in claim 1 wherein the specimen container is a sealable cup.

9. A specimen bottle for water testing comprising:

(a) a bottle section, the bottle section having at least one recess for receiving a heating element and at least one recess for receiving a temperature sensor;

(b) a removable cap for sealing the specimen bottle; and (c) a reagent for microbial testing.

10. A specimen container for water testing comprising:

(a) a container section, the container section having at least one recess for receiving a heating element and at least one recess for receiving a temperature sensor;

(b) a removable cap for sealing the container section; and (c) a reagent for microbial testing.

* * * * *